United States Patent [19]

Batters

[11] Patent Number: 5,038,797
[45] Date of Patent: Aug. 13, 1991

[54] ELECTRICAL STIMULATION TREATMENT DEVICE AND METHOD OF USE

[75] Inventor: Robert C. Batters, College Park, Ga.
[73] Assignee: Romaine, Incorporated, Elkhart, Ind.
[21] Appl. No.: 483,047
[22] Filed: Feb. 20, 1990
[51] Int. Cl.⁵ .................... A61N 1/04; A61L 15/00; A61F 13/02
[52] U.S. Cl. .................................... 128/798; 128/802
[58] Field of Search ............... 128/798, 802, 803, 402, 128/644, 640

[56] References Cited

U.S. PATENT DOCUMENTS

| | | | |
|---|---|---|---|
| 4,377,160 | 3/1983 | Romaine | 128/156 |
| 4,391,278 | 7/1983 | Cahalan et al. | 128/798 |
| 4,404,820 | 9/1983 | Romaine | |
| 4,422,461 | 12/1983 | Glumac | 128/798 |
| 4,624,320 | 11/1986 | Romaine | |
| 4,708,149 | 11/1987 | Axelgaard et al. | 128/798 |
| 4,763,660 | 8/1988 | Kroll et al. | 128/798 |
| 4,771,783 | 9/1988 | Roberts | 128/798 |

FOREIGN PATENT DOCUMENTS

| | | | |
|---|---|---|---|
| 0193480 | 9/1986 | European Pat. Off. | 128/798 |
| 3609536 | 3/1987 | Fed. Rep. of Germany | 128/798 |
| 1299449 | 12/1972 | United Kingdom | |

*Primary Examiner*—Lee S. Cohen
*Assistant Examiner*—Krista M. Pfaffle
*Attorney, Agent, or Firm*—Flynn, Thiel, Boutell & Tanis

[57] ABSTRACT

An improved method and device for electrical stimulation treatment of a body part of a patient. The electrical stimulation treatment device comprises an elongated, flexible, self-supporting, self-adherable strip electrode adapted to be placed in direct surface-to-surface contact with the body part of a patient by being wound around the body part and an electric current source electrically connected to the strip electrode. The strip electrode is an elongated, thin, substantially planar, flexible, permeable substrate which is impregnated and filled with a gel which is capable of adhering to itself.

16 Claims, 2 Drawing Sheets

ELECTRICAL STIMULATION TREATMENT DEVICE AND METHOD OF USE

FIELD OF THE INVENTION

This invention relates to an improved method for electrical stimulation treatment and a treatment device used in this method and, more particularly, to an improved electrical stimulation treatment device which has a flexible strip electrode which is impregnated with a conducting, cooling gel and is adapted to be wrapped around a selected portion of a human or animal body for direct treatment to a sprain, fracture, contusion or bruise.

BACKGROUND OF THE INVENTION

Many bodily injuries, such as sprains, fractures, strains, dislocations, hyperextensions and contusions, are painful and cause substantial discomfort to the injured party due to tissue damage and the resulting hemorrhaging of blood beneath the skin, which in turn causes substantial swelling. Swelling causes the injury to be more painful and disabling and reduces the range of motion of the injured body part. Electrical stimulation treatment is usually the preferred treatment method of reducing the pain and swelling associated with the previously discussed types of injuries.

Electrical stimulation treatment typically comprises the placing of a conducting gel on the injured body part of the site of the injury and the placement of a carbon electrode into contact with the conducting gel so that an electrical current from a voltage stimulator can be applied to the site of the injury. Typically, it is also desirable to also apply cooling to the site of the injury during the electrical stimulation treatment to help reduce swelling.

Accordingly, the present invention relates to an improved electrical stimulation treatment device and method of using this device for treatment of injuries of the above type by electrical stimulation. More specifically, the present invention relates to an improved flexible electrode which can be quickly and easily wrapped around an injured portion of the body to enable the application of direct electrical stimulation treatment thereto. This improved electrode not only permits the direct application of electrical stimulation treatment to the injured body part, it also provides proper compression on and around the injured body portion and permits the cooling of the injured body portion due to both refrigeration and evaporation. This improved electrode also adheres to itself so that it can easily be wrapped around the injured body portion and will securely stay in position without requiring other wraps, ties or fasteners, so that the injured person thus has substantial freedom of movement and may be able to exercise the injured body portion during the electrical stimulation treatment. At the same time, the electrode has substantially total skin contact with a large area of the injured body portion which enables the maximum delivery of electrical stimulation treatment and the maximization of the compression and cooling effects.

Additionally, the improved electrode is clean and nontoxic, and does not stick or adhere to the skin so that the electrode can be easily removed from the injured body portion without causing discomfort or requiring any subsequent cleaning of the skin. The electrode is packagable in a small and compact form because it can be spirally rolled for storage. Additionally, it can be stored in a refrigerator to increase the cooling properties thereof when subsequently applied, it can be readily reused and is low in cost.

The improved electrode of the inventive electrical stimulation treatment device comprises an elongated strip of gel-impregnated material which is self-supporting and self-adhering with the width, thickness and length of the strip being variable according to the injury and the body portion to which the electrode is applied. However, the length of the electrode is selected so as to permit it to be wrapped several times around the injured body area, such as around an ankle, elbow, knee or wrist. The electrode, when applied, is wrapped several times around the injured area so that the various convolutions of the electrode overlap and hence adhere to one another so that the electrode will remain in a wrapped condition without requiring additional clips or ties. The gel-like material of the electrode does not adhere or stick to the skin, but is capable of substantially total surface-to-surface, non-adhering contact with the skin to provide the desired delivery of electrical current, cooling and compression thereto. A gel-like material permits the cooling of the injured body area by evaporation, and the cooling of the injured body area is preferably further assisted by cooling the electrode in a refrigerator prior to its application to the injured body area. The gel-like material of the electrode preferably is formed by gelling a polyvinyl alcohol solution formed from approximately 6 parts or more of polyvinyl alcohol per 100 parts of water. A sheet or strip of a thin, nonwoven polyester fabric is dipped in the polyvinyl alcohol solution, and thereafter dipped in a reactive gelling agent solution, such as an aqueous borax solution, to form a gel. The polyvinyl alcohol gel also preferably has another ingredient, such as glycerin, incorporated therein so as to make the resulting gel material more pressure-sensitive at lower temperatures, such as at refrigeration temperatures, for example, about 1° to 5° C. The polyester fabric functions as a central core or carrier for providing the electrode with increased strength and continuity so as to thereby facilitate handling of the electrode and to prevent accidental tearing of the electrode during handling and usage thereof. The electrode is electrically connected to a conventional portable high-voltage stimulator or low-voltage transcutaneous electrical nerve stimulator to form the device of the present invention. Other objects and purposes of the invention will be apparent after reading the following specification and inspecting the accompanying drawings.

DETAILED DESCRIPTION OF THE INVENTION

Figure 1:
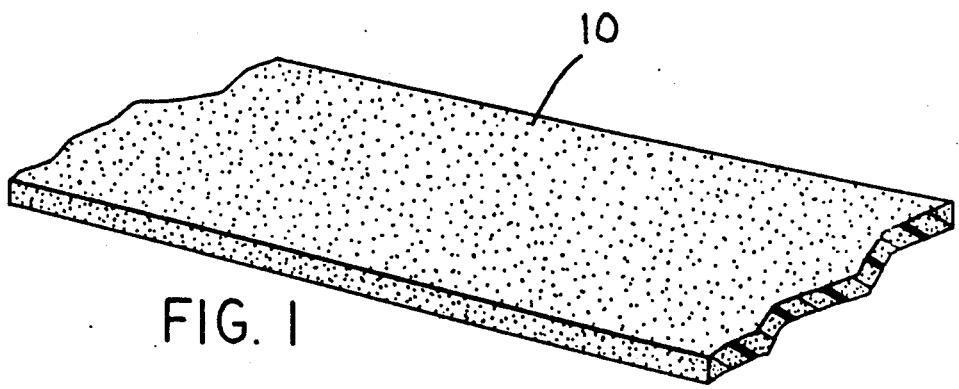
FIG. 1 is a perspective view of a fragment of the electrode.
Figure 2:
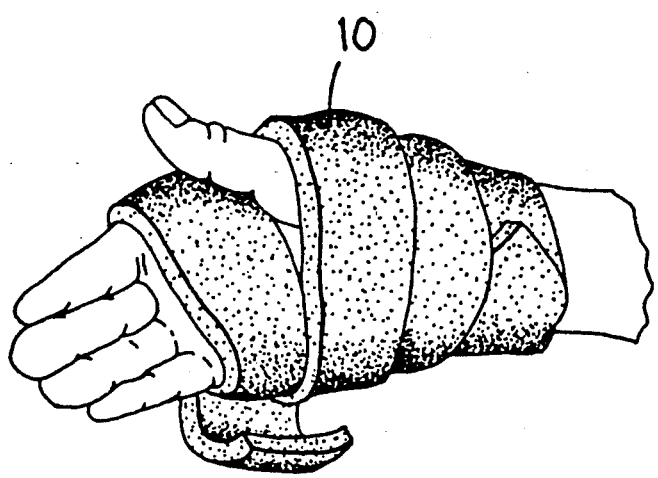
FIG. 2 illustrates one manner of use for the electrode, namely, wrapping the electrode around an injured hand or wrist.
Figure 3:
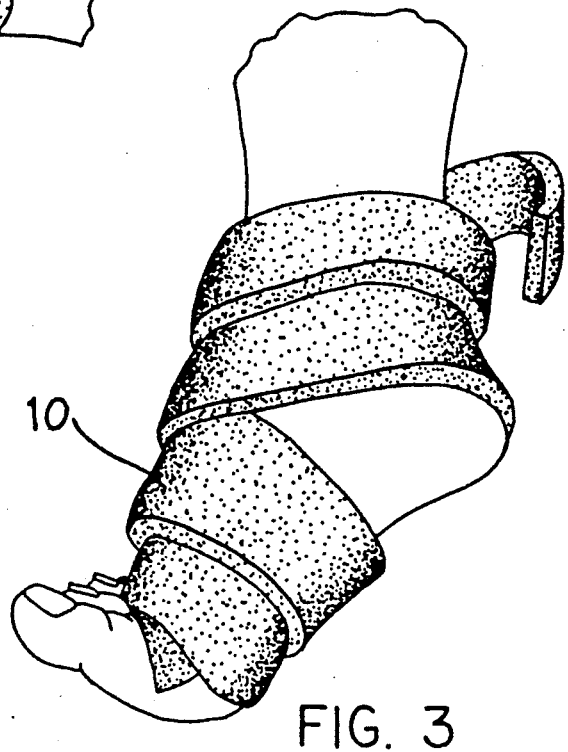
FIG. 3 illustrates another use of the electrode for wrapping same around an injured ankle or foot.

Referring to the drawings, FIG. 1 illustrates a fragment of a strip electrode 10 according to the present invention. The strip electrode 10 is an elongated, flexible, pliant, flat strip which is adapted to be wrapped around a part of a human or animal body, such as the wrist and hand (FIG. 2), the foot and ankle (FIG. 3) or an arm (FIG. 5) in order that electrical stimulation treatment, compression and cooling can be applied to that body part. The opposite surfaces of the strip electrode are self-adherent to one another so that the contacting surface portions of the turns or convolutions of the electrode releasably adhere to each other whereby the strip electrode will remain in place on the human or animal body part until it is removed. Although a separately applied adhesive can be applied between the contacting surfaces of the electrode to obtain the above-described adhesion, it is preferred, for convenience in use, to make the opposite surfaces of the electrode self-adhering. It is preferred that the self-adherent properties of the electrode be such that the bond strength at the adhesive joint is less than the strength of the electrode itself in order that removal of the electrode will be achieved by adhesive bond failure at the adhesive joint, rather than cohesive failure of the material of which the electrode is made, in order that the electrode will not be destroyed when it is removed. The electrode 10 does not significantly adhere to the skin of the human or animal part so that the electrode can easily be removed from the body part by a simple unwrapping or peeling procedure, without causing injury or discomfort to the skin or requiring significant cleaning of the skin.

The electrode 10 preferably is somewhat elastically elongatable so that it can be moderately stretched when it is applied to the body part in order to apply the moderate compression onto the body part around which it is wrapped. For this purpose, the electrode 10 has an elastic elongation of at least about 10 percent and, preferably, in the range of from 25 to about 75 percent.

The thickness, flexibility and pliability of the electrode 10 are devised so that when the electrode is wrapped around the part of the human or animal body, it will conform closely to the contour of that body part in order that substantially the entire inner surface of the electrode will be in surface-to-surface contact with that body part, except for the regions of the electrode where edge portions of adjacent turns thereof are overlapped with one another. The thickness of the electrode is ordinarily in the range of about 3/16 to about 10/16 inches, preferably about ½ inch. The width of the strip electrode is selected so that the body part can be completely wrapped by making only a few turns of the electrode around the body part. Thus, for applying the electrode strip to the extremities of a human body, such as a hand or foot, the width of the electrode is from about 1 inch to about 4 inches, preferably about 3 inches. The length of the electrode is selected so as to be effective to wrap the entire area of a human or animal body part to which the electrode is to be applied. For example, the length of the electrode can be from about 4 inches to about 6 feet.

The electrode 10 is made preferably of a nonwoven polyester fabric having a rating in the range of about 2 to about 4 ounces per square yard. The electrode 10 is impregnated with a high water content gel which is capable of adhering to itself but which does not, however, adhere strongly to human or animal skin. While in contact with the skin, the electrode will cool the skin by evaporative cooling during the electric stimulation treatment. The cooling effect can be enhanced by refrigerating the electrode 10 in advance. For example, the electrode can be kept in a refrigerator, at about 1° to 5° C., until it is to be used. Additionally, the electrode 10 can be cooled by water rinsing.

Figure 4:
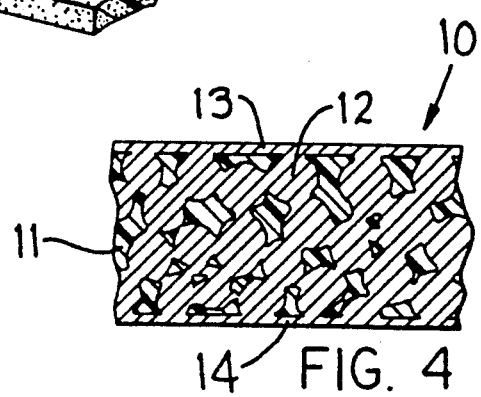
FIG. 4 is a cross-section of a fragment of the electrode.

Referring to FIG. 4, the flexible, nonwoven polyester material 11 functions as a carrier or a porous substrate for holding the gel 12. The gel 12 penetrates into and substantially fills the pores of the polyester material 11 and the gel also forms thin integral surface layers 13 and 14 which substantially completely cover the opposite surfaces of the polyester material. The gel layers 13 and 14 are self-adherent to each other but they do not strongly adhere to the skin.

The gel 12 is obtained by gelling an aqueous solution of polyvinyl alcohol which has previously been impregnated into the polyester material 11. The gel 12 is formed, in situ, in the polyester material 11, by gelling an aqueous solution consisting essentially of about 4 to about 8 weight percent, preferably from about 5 to about 7 weight percent, of polyvinyl alcohol, and the balance is essentially water. It is well known that aqueous solutions of polyvinyl alcohol are coagulated by contacting same with the various inorganic and organic compounds. As inorganic compounds, there can be mentioned sodium borate, sodium carbonate, ammonium sulfate, sodium sulfate, potassium sulfate, aluminum sulfate, zinc sulfate, etc. As typical organic compounds capable of coagulating polyvinyl alcohol, there can be mentioned Congo Red, resorcinol, direct azo dyes, etc. It is preferred to use sodium borate (borax) as the agent for gelling the polyvinyl alcohol aqueous solution employed in the invention because sodium borate is capable of rapidly insolublizing the polyvinyl alcohol by a chemical crosslinking action. For example, treatment of the polyester material 11 previously impregnated with the polyvinyl alcohol aqueous solution, with an aqueous solution containing from about 2 to about 5 weight percent of sodium borate, will rapidly gel the polyvinyl alcohol in order to insolubilize same and to trap or occlude the water therein.

Gellable polyvinyl alcohol solutions can be prepared by dissolving polyvinyl alcohol in water in accordance with conventional practices. Polyvinyl alcohols having various degrees of hydrolysis are commercially available from various manufacturers, for example, Gelvatol polyvinyl alcohols are commercially available from Monsanto and Vinol polyvinyl alcohols are commercially available from Air Products and Chemicals, Incorporated. The typically commercially available polyvinyl alcohols have a degree of polymerization from about 300 to about 2000 and a degree of hydrolysis (%) of about 88 to about 100 percent.

It is preferred to use a mixture of polyvinyl alcohols having different degrees of hydrolysis in order to prepare the gel, according to the invention. For example, it is preferred to use a mixture (1) from about 20 to about 30 weight percent, preferably about 25 weight percent, of polyvinyl alcohol having a degree of hydrolysis of 98 percent or more, and correspondingly, (2) from 80 to 70 weight percent, preferably about 75 weight percent, of polyvinyl alcohol having a degree of hydrolysis of about 87 to 90 percent. The use of such a mixture is advantageous because it provides a commercially satisfactory rapid rate of gel formation and it presents exudation of water from the gel.

The strip electrode 10 can be easily prepared by immersing the polyester material 11 in a bath of an aqueous solution of polyvinyl alcohol so that the polyester material becomes substantially completely impregnated with the aqueous polyvinyl alcohol solution and forms the thin surface layers 13 and 14 thereon. Then, the impregnated polyester material is dipped in an aqueous solution of the coagulating agent, such as sodium borate, so as to transform the polyvinyl alcohol solution into a gel throughout the polyester material 11 and surface layers 13 and 14.

In order to improve the self-adhering, pressure-sensitive characteristics of the gel 12, and the electrode according to the present invention, particularly in the surface layers 13 and 14 thereof, it is very advantageous to plasticize at least those surface layers by incorporating a plasticizing material therein. Inasmuch as the self-adhering, pressure-sensitive properties are essentially needed only for the surface layers 13 and 14 and such plasticization is not required in the portions of the gel contained within the body of the polyester material 11, it will be sufficient to incorporate a plasticizer in the gelling agent aqueous solution so that the plasticizer migrates into and plasticizes at least the surface layers 13 and 14 of the gel as the gel is formed in situ in the polyester material.

As the plasticizer, it is preferred to use glycerol because of its high compatibility with polyvinyl alcohol and its effectiveness in imparting the pressure-sensitive property of the polyvinyl alcohol gel. Moreover, because of its relatively high boiling point and low volatility, glycerol is an effective material for practical use. The glycerol prevents the polyvinyl alcohol from becoming hard and brittle at low humidities. Further, the presence of the glycerol improves the tensile elongation of the surface layers 13 and 14. It is effective to incorporate up to about 10 percent, preferably about 5 percent of glycerol, in the aqueous gelling agent solution that is used to gel the aqueous polyvinyl alcohol solution. If desired, an effective amount of a compatible antiseptic can be incorporated into the gel to prevent deterioration of the gel by microorganisms. An iodine-type antiseptic, such as Amical No. 48 (Abbott Laboratories) is preferred.

Figure 5:
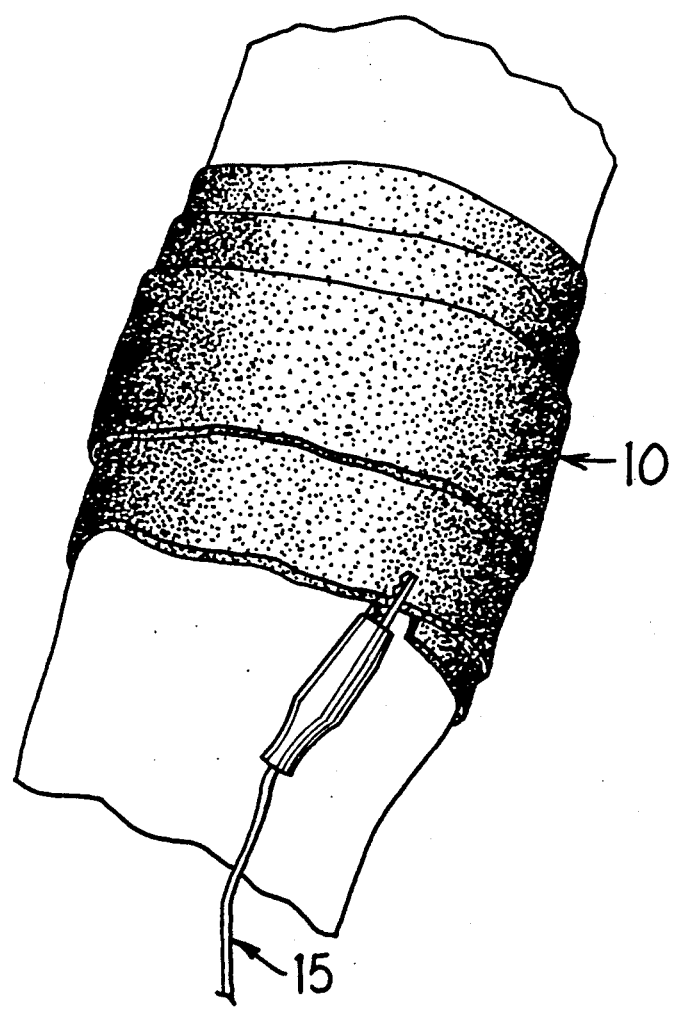
FIG. 5 is a perspective view of the electrode wrapped around an injured arm and an alligator clip connecting the electrode with a voltage stimulator.

As illustrated in FIG. 5, in use, the strip electrode 10 is wrapped around the desired body part to be treated and an electrical connection means 15, such as an alligator clip, is attached to the strip electrode 10 and a voltage stimulator (not shown). The clip 15 is preferably placed between adjacent convolutions of the strip electrode 10. Any commercially available voltage stimulator can be used in the present invention. For low voltage stimulation, a transcutaneous electrical nerve stimulator (TENS) unit, such as Tenzcare by 3M, may be used. Electrical stimulation treatment with such a TENS unit is generally in the range of from about 1–22 volts and from 1–3 milliamps. For high voltage treatment, a high-voltage stimulator, such as a Varapulse stimulator, by Staodynamics, may be used. This high-voltage stimulator typically operates between 1 and 500 volts and a current range of from abut 1–100 milliamps.

The efficacy of the present invention is illustrated in the following discussion.

A clinical study was performed over a three-month period in which 35 patients, ranging in age from 16 to 82 years of age, were given electrical stimulation treatment by the present invention. The objects of the treatments were to ascertain if a decrease in pain, swelling or an increase in range of motion resulted as the result of the treatment with the present invention. Nine of the patients had problems involving swelling of the ankle in which volumetric measurements were taken before and after the treatment. These volumetric measurements were made by the displacement method in which the amount of water displaced from a container was measured before and after the treatment. Each treatment lasted between 20 and 30 minutes. If range of motion was a desired goal, the patients performed active and active-assistive motion exercises with the strip electrode in place. Electrical stimulation was provided by either a portable high-voltage stimulator or a low-voltage TENS unit stimulator.

Five different sizes and shapes of electrodes were used. The pain relief was measured on a subjective scale of 1 to 10 with the patients being asked to score their before-treatment pain as a 10, and then to rate the after-treatment pain in comparison to the before-treatment pain. The following table illustrates the results of this clinical study.

TABLE

| Diagnosis | Patents Treated | Size of Electrode | Pain Relief 10-0* | Gain in Range of Motion | Volume of Fluid Removal |
|---|---|---|---|---|---|
| Arthromenisectomy | 1 | 4" × 48" | 3-4 | 88°-110° | N/A |
| | 1 | 4" × 48" | 2 | 130°-137° | N/A |
| Anterior Curciate | 1 | 4" × 48" | 1 | N/A | N/A |
| Ligament Reconstruction | 1 | 4" × 48" | 0 | 85°-110° | N/A |
| | 1 | 3" × 72" | 3 | 10°-FL | N/A |
| Ankle Sprain (3-Day) | 1 | 3" × 24" | % | N/A | N/A |
| (6-Day) | 1 | 3" × 14" | — | 30° In/Ev 25° Dorsi | 95 ml |
| Acute Ankle Sprain | 1 | 3" × 14" | 8 | 20° Dorsi Flexion | 198 ml |
| | 1 | 3" × 14" | 2 | 30° Dorsi & Plantar FL | — |
| | 1 | 3" × 72" | 2 | 10° Plantar & Dorsi | — |
| | 1 | 3" × 48" | 4 | 30° Plantar FL, 20° Dorsi | 20 ml |
| Ankle Sprain | 1 | 3" × 14" | 3 | 20° | — |
| | 1 | 3" × 14" | 5 | N/A | N/A |
| Fractured Cuboid (foot) (2 hours old) | 1 | 3" × 24" | 2 | N/A | N/A |
| Medial Collateral | 1 | 3" × 72" | 9 | 0 | N/A |

TABLE-continued

| Diagnosis | Patents Treated | Size of Electrode | Pain Relief 10-0* | Gain in Range of Motion | Volume of Fluid Removal |
| --- | --- | --- | --- | --- | --- |
| Ligament Strain | | | | | |
| Medial Collateral | 1 | 3" × 72" | 0 | 15° Flexion | N/A |
| Ligament Tear | 1 | 3" × 72" | 0 | 27° Flexion | N/A |
| | 1 | 3" × 72" | 2 | 10° Flexion | N/A |
| Anterior Curciate Ligament Tear | 1 | 3" × 72" | 5 | 10° Knee Flexion | — |
| | 1 | 3" × 72" | 0 | 25° Knee Flexion | — |
| | 1 | 3" × 72" | 0 | 20° Flexion | — |
| Tibial Osteotomy | 1 | 4" × 48" | 1 | Full | N/A |
| Fractured Neck Humerus | 1 | 3" × 14" | 4 | 30° FL, 20° Ext | N/A |
| Fractured Tibia | 1 | 3" × 72" | 2 | 10° Ext | — |
| | 1 | 3" × 72" | 4 | 5° FL | — |
| Fractured R Humberus | 1 | 3" × 72" | 0 | 5-10° FL & Abduction | N/A |
| | 1 | 3" × 14" | 2 | — | — |
| Lumbo Sacral Strain | 1 | 3" × 14" | 0 | — | — |
| Pes Anserine Bursitis | 1 | 3" × 14" | 5 | — | — |
| Achilles Tendinitis | 1 | 3" × 14" | 4 | 10° Plantar, 10° Dorsi | — |
| Lateral Epicondylitis | 1 | 3" × 12" | 8 | — | — |
| | 1 | 3" × 12" | 6 | — | — |
| Chondromalcia Patella | 1 | 3" × 72" | 3 | — | — |
| Avulsion Fracture Foot | 1 | 3" × 72" | 0 | 10° Plantar, 15° Dorsi | 152 ml |
| Post Op Arthromenisctomy | 1 | 3" × 72" | 5 | — | — |

*Before-treatment pain was recorded at 10. After treatment pain score follows.

As seen by the results illustrated in the table, the electrical stimulation treatment device of the present invention performed extremely well during clinical testing. The patients reported a significant decrease in pain because of treatment with the present invention and in the patients where volumetric studies were performed, the average amount of fluid removed from the foot and ankle was 98.76 milliliters. It was noted that the earlier the treatment was performed after the injury, the greater the volume of fluid removed. With the strip electrode of the present invention, no burns or "hot spots" resulted from the treatment. Also, the strip electrode could be used in 12 to 15 applications without a loss in effectiveness, which makes the use of the strip electrode cost effective.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. An electrical stimulation treatment device comprising: an elongated, flexible, self-supporting, self-adherable strip electrode adapted to be placed in direct surface-to-surface contact with a body part of a patient by being wound around said body part, said strip electrode being of a length sufficient to allow it to be wrapped totally around the body part with its adjacent convolutions being overlapped and adhered to one another so that the strip electrode will remain wrapped around the body part, said strip electrode consisting essentially of an elongated, thin, substantially planar, flexible, permeable substrate which is impregnated with a gel, said gel containing from about 4 to 8 weight percent of polyvinyl alcohol and the balance being essentially water, said polyvinyl alcohol being coagulated with a coagulating agent to insolubilize said polyvinyl alcohol and trap the water therein, said gel being capable of adhering to itself and extending to opposite surfaces of said substrate so that said strip electrode is pressure-sensitive and will adhere to itself and can be unwound and removed from the body part without leaving a significant amount of residue thereon; current transmission means for transmitting an electrical current from an electrical current source to said strip electrode; and said electrical current source.

2. A treatment device as claimed in claim 1, wherein said substrate comprises a synthetic resin.

3. A treatment device as claimed in claim 2, wherein said synthetic resin is a polyester resin.

4. A treatment device as claimed in claim 1, wherein said strip is nontoxic and nonmedicated.

5. A treatment device as claimed in claim 1, wherein said opposite surfaces of said substrate comprise a plasticizer in an amount effective to increase the tack of said gel.

6. A treatment device as claimed in claim 5, wherein said plasticizer is glycerol.

7. A treatment device as claimed in claim 1, wherein said strip electrode has a thickness of from about 3/16 to about 10/16 inches, a width of from about 1 inch to about 4 inches and a length of from about 4 inches to about 6 feet.

8. A method for applying electrical stimulation to a body part of a patient comprising the steps of:
wrapping an elongated, flexible, self-supporting, self-adherable strip electrode around the body part, said strip electrode being adapted to be placed in direct surface-to-surface contact with the body part and being of a length sufficient to allow it to be wrapped totally around the body part with its adjacent convolutions being overlapped and adhered to one another so that the strip electrode will remain wrapped around the body part, said strip electrode consisting essentially of an elongated, thin, substantially planar, flexible, permeable substrate which is impregnated with a gel, said gel containing from about 4 to 8 weight percent of polyvinyl alcohol and the balance being essentially water, said polyvinyl alcohol being coagulated with a coagulating agent to insolubilize said polyvinyl alcohol and trap the water therein, said gel being capable of adhering to itself and extending to opposite surfaces of said substrate so that said strip electrode is pressure-sensitive and will adhere to itself and can be unwound and removed from the body part without leaving a significant amount of residue thereon;

attaching said strip electrode to a source of an electric current; and applying an electric current to said strip electrode to treat said body part.

9. A method as claimed in claim 8, additionally comprising the step of cooling said strip electrode before it is wrapped around the body part.

10. A method as claimed in claim 9, wherein said strip electrode is cooled by water rinsing.

11. A method as claimed in claim 8, additionally comprising the step of cooling said strip electrode after it is removed from the body part.

12. A method as claimed in claim 11, wherein said strip electrode is cooled by water rinsing.

13. A method as claimed in claim 8, additionally comprising the step of storing said strip electrode in a refrigerator after it is removed from the body part.

14. A method as claimed in claim 8, wherein said electric current is in the range of 1-3 milliamps.

15. A method as claimed in claim 8, wherein said electric current is in the range of 1-100 milliamps.

16. A method as claimed in claim 8, wherein said body part is exercised during said electrical stimulation treatment.

* * * * *

UNITED STATES PATENT AND TRADEMARK OFFICE
CERTIFICATE OF CORRECTION

PATENT NO.  : 5 038 797
DATED       : August 13, 1991
INVENTOR(S) : Robert C. BATTERS It is certified that error appears in the above-identified patent and that said Letters Patent is hereby corrected as shown below:

Col. 6, line 56:
In the table, in the column entitled "Pain Relief 10-0*", 6th line down, change "%" to ---5---.

Signed and Sealed this

Thirtieth Day of March, 1993

Attest:

STEPHEN G. KUNIN

Attesting Officer       Acting Commissioner of Patents and Trademarks